United States Patent
Noice et al.

(10) Patent No.: US 7,094,219 B2
(45) Date of Patent: Aug. 22, 2006

(54) INTRAVENOUS FLUID WARMING DEVICE

(75) Inventors: Frank M. Noice, So. Pasadena, CA (US); Christl Diane Treptow, Vista, CA (US); David Thomas Treptow, Vista, CA (US)

(73) Assignee: The Heat Factory, Inc, Vista, CA (US)

(*) Notice: Subject to any disclaimer, the term of this patent is extended or adjusted under 35 U.S.C. 154(b) by 732 days.

(21) Appl. No.: 10/346,042

(22) Filed: Jan. 15, 2003

(65) Prior Publication Data

US 2003/0163087 A1    Aug. 28, 2003

Related U.S. Application Data

(60) Provisional application No. 60/348,571, filed on Jan. 15, 2002.

(51) Int. Cl.
*A61F 7/12* (2006.01)

(52) U.S. Cl. .................... 604/113
(58) Field of Classification Search ................ 604/113, 604/114, 251, 255, 257, 262, 264, 272, 523; 126/204, 206, 263.01, 263.02; 601/1, 3, 601/15–17

See application file for complete search history.

(56) References Cited

U.S. PATENT DOCUMENTS

| | | | | |
|---|---|---|---|---|
| 4,077,390 A | * | 3/1978 | Stanley et al. | 126/263.04 |
| 4,572,158 A | * | 2/1986 | Fiedler | 126/263.04 |
| 4,934,336 A | | 6/1990 | White | 126/263 |
| 4,976,685 A | * | 12/1990 | Block, Jr. | 604/522 |
| 5,042,455 A | | 8/1991 | Yue et al. | 126/263 |
| 5,046,479 A | | 9/1991 | Usui | 126/204 |
| 5,250,032 A | | 10/1993 | Carter, Jr. et al. | 604/113 |
| 5,254,094 A | * | 10/1993 | Starkey et al. | 604/113 |
| 5,527,293 A | | 6/1996 | Zamierowski | 604/176 |
| 5,601,894 A | * | 2/1997 | Maruschak | 428/36.9 |
| 6,464,666 B1 | | 10/2002 | Augustine et al. | 604/113 |

FOREIGN PATENT DOCUMENTS

WO   PCT/US03/01335    7/2003

* cited by examiner

*Primary Examiner*—LoAn H. Thanh
(74) *Attorney, Agent, or Firm*—K. David Crockett, Esq.; Crockett & Crockett

(57) ABSTRACT

A device for warming fluids being administered intravenously to a patient. The heating assembly comprising a warming pouch is wrapped and secured around a tube through which fluid is intravenously provided to the patient.

26 Claims, 3 Drawing Sheets

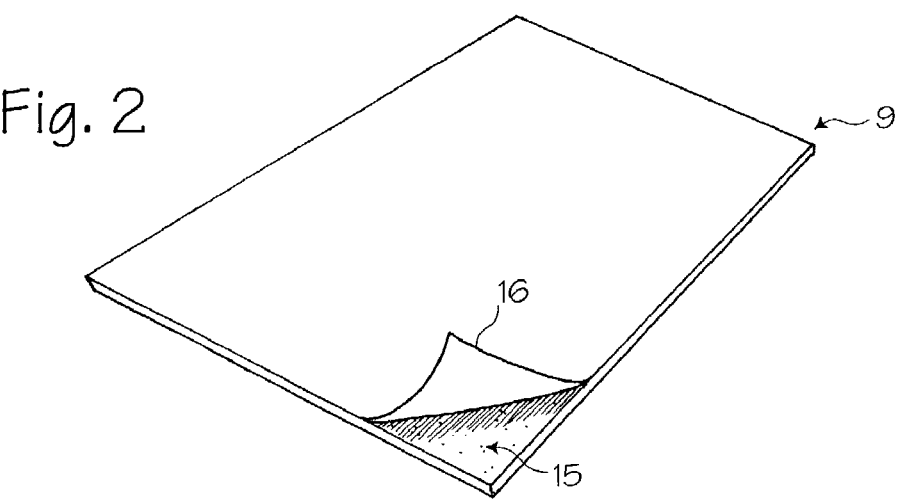
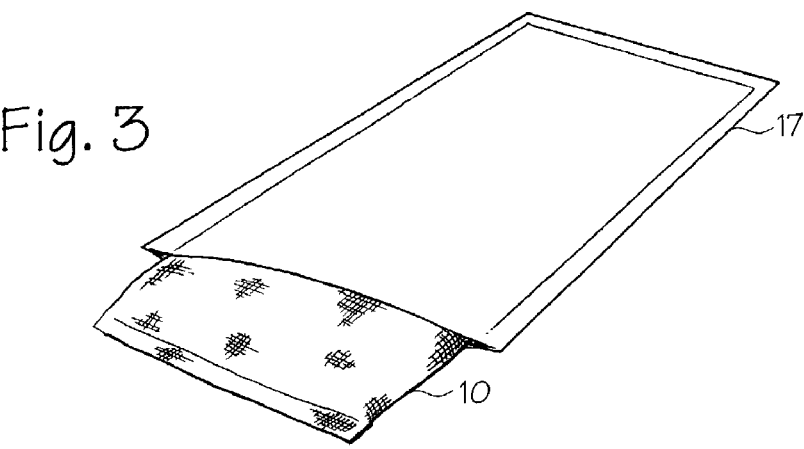
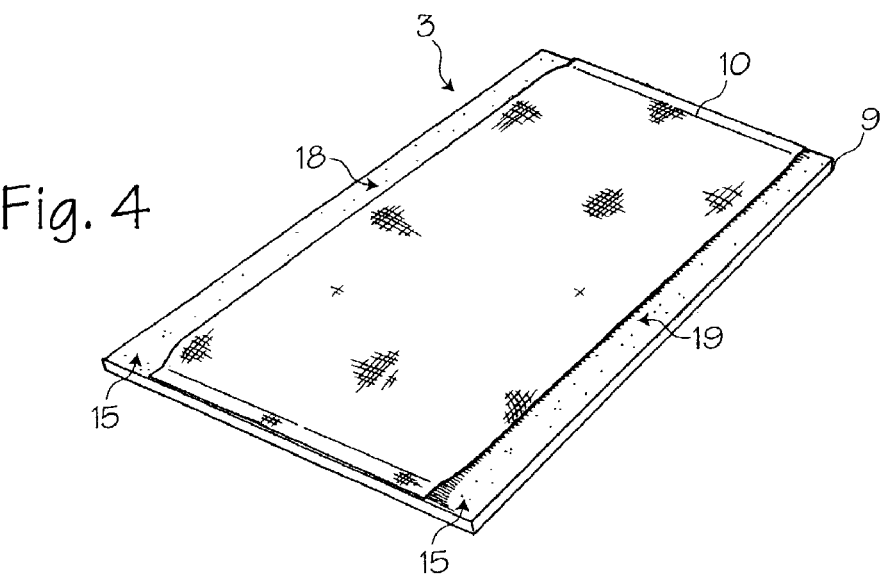

INTRAVENOUS FLUID WARMING DEVICE

This application claims priority to U.S. Provisional Application No. 60/348,571, filed Jan. 15, 2002.

FIELD OF THE INVENTIONS

The inventions described below relate the field of devices that warm fluids delivered to patients.

BACKGROUND OF THE INVENTIONS

Hypothermia, which comprises a body temperature of 95° F. or below, is a serious condition for which all trauma patients are at risk. Due to the use of anesthetics and the administration of cold intravenous fluids, 65% of all surgical patients experience hypothermia. Hypothermia causes discomfort and can cause potentially life-threatening complications, such as ventricular fibrillation, especially during surgery.

In an operating room setting, fluid may be provided to a trauma patent at flow rates varying from 20 ml per minute to 1 liter per minute. Fluid to be provided intravenously flows through a plastic tube extending from a fluid reservoir (such an intravenous bag) to a vein within the patient. The intravenous bag is typically stored or held in the operating room, and when administered to the patient, it is administered through a tube which may be 6 to 8 feet long. Operating rooms are usually maintained at about 55° F. to about 65° F. degrees, and, consequently, any fluid in the intravenous bag is often cooled to the ambient temperature which is well below body temperature. Infusing this cold fluid intravenously into the already stressed surgical patient can significantly affect the patient's body temperature and greatly increase the chances that the patient will experience hypothermia and other serious complications.

Hypothermia and other deleterious effects of cold IV fluids can be avoided by heating the IV fluid. However, even with the current, overwhelming evidence of the clinical benefits of fluid warming (which includes avoidance of hypothermia, discomfort, shivering, and reduced infection rates, faster healing, shortened hospital stays, and reduced risk of serious heart injury), only about 4% of the 45 million U.S. hospital infusions were warmed during the year 2000. Almost none of the 4 million emergency infusions were warmed. Thus, a simple, cost effective device is needed to warm fluids provided intravenously to patients.

Heating may be accomplished prior to use, but this may be impractical in an emergency settings or field applications. Thus, heating may be advantageously accomplished during the administration of the intravenous fluid, through heat exchange between the intravenous fluid and a heat source placed in the intravenous flow path. Several devices have been proposed for use in warming intravenous fluid. Kistner, Intravenous Warming System, U.S. Pat. No. 6,139,528 (Oct. 31, 200) discloses an electrical heating system, where intravenous fluid passes through a heat exchanger and is heated by electrical heating elements. White, Apparatus and Method for Warming Intravenous Equipment, U.S. Pat. No. 4,934,336 (Jun. 19, 1990) discloses a system in which flexible containers holding crystalizable supercooled aqueous salt solution are packed around an IV bag and the proximal extent of the IV tube.

SUMMARY

The devices and methods described below provide for a means for warming fluids provided intravenously to patients. A warming pouch is disposed around an IV tube, at its distal extent, within several inches of the distal tip of the catheter (that part which is inserted into a vein of the patient) and the percutaneous entry point. Where a drip chamber is used, the warming pouch is disposed on the IV tube between the entry point and the drip chamber.

In one embodiment, the system is assembled just prior to use by removing the warming pouch from the airtight package, applying a slightly oversized adhesive sheet to one side of the pouch, and then folding the pouch over the IV tube and securing the pouch around the tube with that portion of the adhesive sheet that extends over the margins of the pouch. In another embodiment, the pouch is manufactured with an adhesive surface, and is stored with a peel-away sheet protecting the adhesive. To use the warming pouch of this embodiment, the warming pouch is removed from its airtight package, the protective sheet is peeled away, and the adhesive side of the pouch is folded over the IV tube and folded against itself to secure the pouch onto the IV tube.

BRIEF DESCRIPTION OF THE DRAWINGS

FIG. 2 shows an adhesive sheet for use in intravenous fluid warming and infusion system shown in FIG. 1.

FIG. 3 shows the warming pouch for use in intravenous fluid warming and infusion system shown in FIG. 1.

FIG. 4 shows the warming pouch disposed on the adhesive sheet.

DETAILED DESCRIPTION OF THE INVENTIONS

Figure 1:
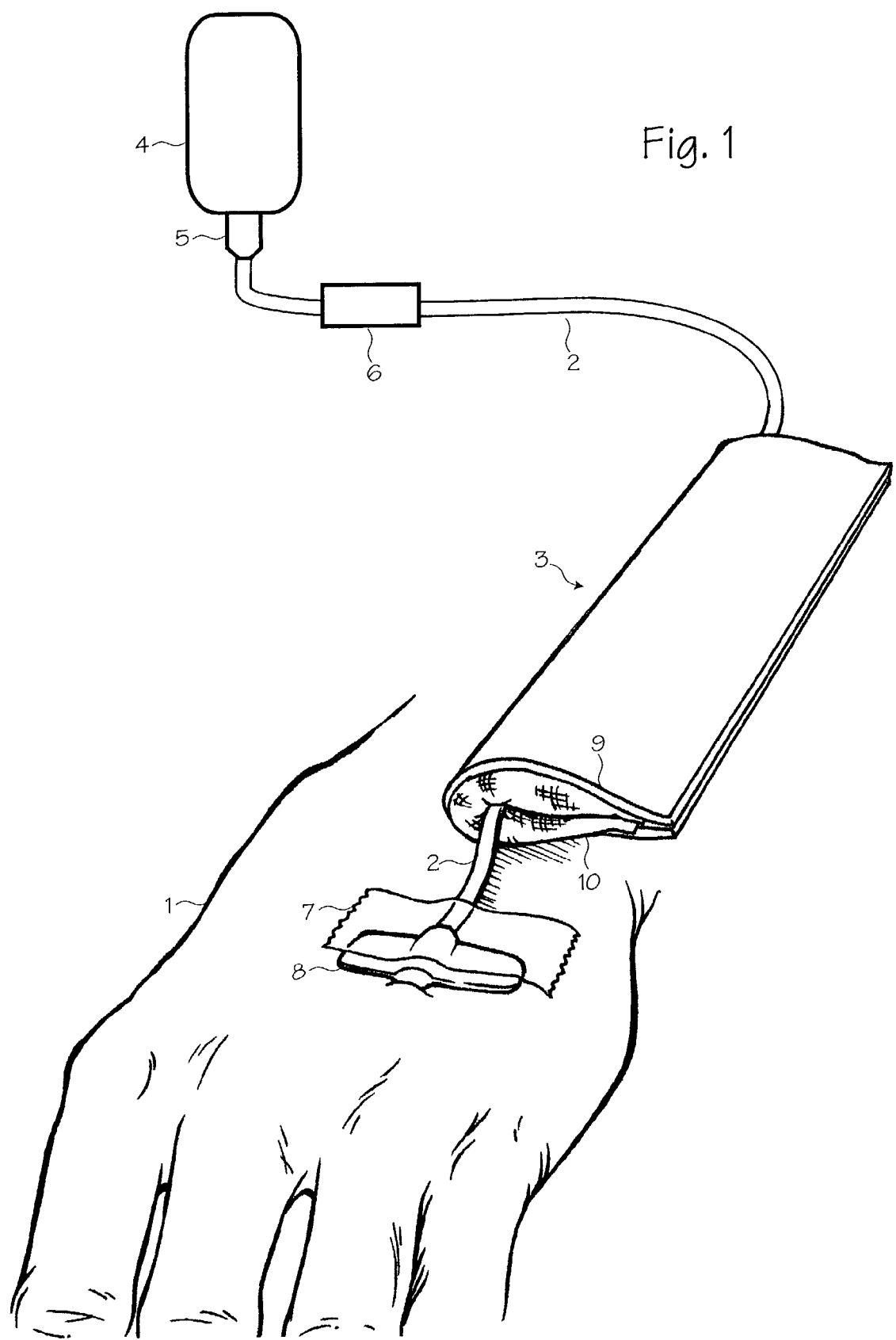
FIG. 1 shows the intravenous fluid warming and infusion system in place on a patient.

FIG. 1 shows the intravenous warming and infusion system installed on a patient 1. The system comprises an intravenous catheter or IV tube 2 and a heating assembly 3 wrapped around the tube. The fluid is stored in an intravenous bag 4 and the bag is in fluid communication with the tube through a drip chamber 5 and a roller clamp 6 which is used to control the infusion rate. The tube is secured to the patient with tape 7 and the tube is in fluid communication with the vein either directly or through a hollow needle connected to the tube, with the distal tip of the tube or the needle disposed within the vein. A fixation assembly 8 may also be provided to inhibit twisting of the IV tube near the percutaneous entry point.

The heating assembly comprises an adhesive sheet 9 disposed around a warming pouch or pad 10. In the assembled form, the adhesive sheet forms an outer covering, and the pouch forms an inner covering, for a warming medium. The warming pouch contains an exothermic composition capable of producing an exothermic reaction and thus producing heat. Most conveniently, the warming pouch comprises an air-permeable pouch filled with an "exothermic composition" comprising an aggregate of materials that react with oxygen in the air to produce heat. The common iron powder, cellulose (sawdust), vermiculite, and salt aggregate used in recreational pocket warmers is suitable. When exposed to the air the ingredients combine to induce a rapid oxidation of the iron powder which produces heat. The amount of heat produced, the temperature achieved and the longevity of the warming pouch can be controlled by adjusting the formulation of the aggregate. Typically, pouches may produce significant heat for hours. The warming pouch is stored in an airtight package for storage, and is removed from the airtight package immediately prior to use.

The heating assembly 3 is folded around the tube 2 and secured in a longitudinal region of the tube which is about 1 to 6 inches proximal to the point where the tube (or a hollow needle in fluid communication with the tube) enters the patient's vein or from the distal end of the IV tube. Thus, only about 1 to 6 inches of IV tube remains exposes distal to the heating assembly.

FIG. 2 shows the outer covering or adhesive-sheet 9. The adhesive sheet may comprise different flexible materials that are air-permeable and suitable for securing the a warming pouch, such as polypropylene fabric, cotton, and many other fabrics. The adhesive sheet may be provided in different sizes and shapes to accommodate different sizes and shapes of warming pouches. For example, an adhesive sheet of about 3 by 5 inches (7.5 to 12.5 cm) would be suitable for a warming pouch of about 2 by 5 inches (5 by 12.5 cm), as illustrated below. One side of the adhesive sheet is provided with an adhesive 15. The adhesive may be covered with a paper overlay or a release paper 16, which is peeled off at the time of use.

FIG. 3 shows the warming pouch 10 which serves as an inner container for the exothermic composition for use in the intravenous fluid warming and infusion system shown in FIG. 1. The warming pouch is stored in an airtight package 17. In use, the warming pouch 10 removed from the package and exposed to air. The inner container may measure about 2 by 5 inches (5 by 12.5 cm), may be about ¼ inch (roughly 0.5 cm) thick, for use with the adhesive sheet described above. The inner container may comprise other flexible materials that are ventilated or air-permeable.

The exothermic composition may comprise iron powder, cellulose, activated carbon, vermiculite and salt, though the exothermic composition may comprise other combinations of chemicals or substances that produce heat when exposed to air. The composition may also comprise a metal powder, a salt and water. The composition may also comprise an alkaline earth metal oxide, water and a salt. The exothermic composition may have different proportions of ingredients to alter the amount of heat produced.

During manufacturing, the specified ingredients are mixed together and sealed in the inner container. The inner container is then stored in the airtight package, which is sealed to prevent oxygen from reaching the inner container. Just prior to use the airtight package is unsealed and the inner container is exposed to air. The iron dust among the ingredients then oxidizes and generates heat. The amount of heat generated is controlled by the amount of iron powder and other compounds in the exothermic composition, by the permeability of the inner container and by the dimensions of the inner container. The temperature of the warming pouch will be from about 100° F. to about 140° F. during the chemical reaction. When the inner container is wrapped around the tube, the heat will substantially warm the fluid passing through the tube. Warming to a temperature of about 90° F. to 95° F. or higher may be accomplished. The warmer fluid prevents the patient from experiencing hypothermia. The warming device will maintain its maximum temperature for about 3 to about 8 hours, depending on the exothermic composition and the length of the warming device. The shelf life of the exothermic composition within inner container is about 3 years.

FIG. 4 shows the warming pouch 10 disposed on the adhesive sheet 9. To assemble the heating assembly 3 the warming pouch is removed from the airtight package. The release paper 16 on the adhesive sheet is also removed. The warming pouch is then placed on the adhesive-surface of the adhesive sheet to form the heating assembly 3. The warming pouch may be placed on the adhesive sheet such that a strip of adhesive remains exposed on either side of the warming pouch. In one embodiment a first strip 18 of adhesive is about ½ inch (1.25 cm) wide and a second strip 19 of adhesive is also about ½ inch (1.25 cm) wide. The heating assembly is then-folded around the intravenous tube with the inner container facing the tube. The first adhesive strip 18 may be affixed to the second adhesive strip 19 as the assembly is wrapped around the tube 2, thus securing the assembly around the tube. The heating assembly may be assembled immediately prior to use, or it may be manufactured as shown and provided to end-users in the assembled configuration, with appropriate release paper covering the adhesive borders and appropriate airtight packaging protecting the warming pouch from exposure to air. The heating assembly and IV tube can also be provided to end users in a prefabricated assembly including the IV tube and the warming assembly.

Figure 5:
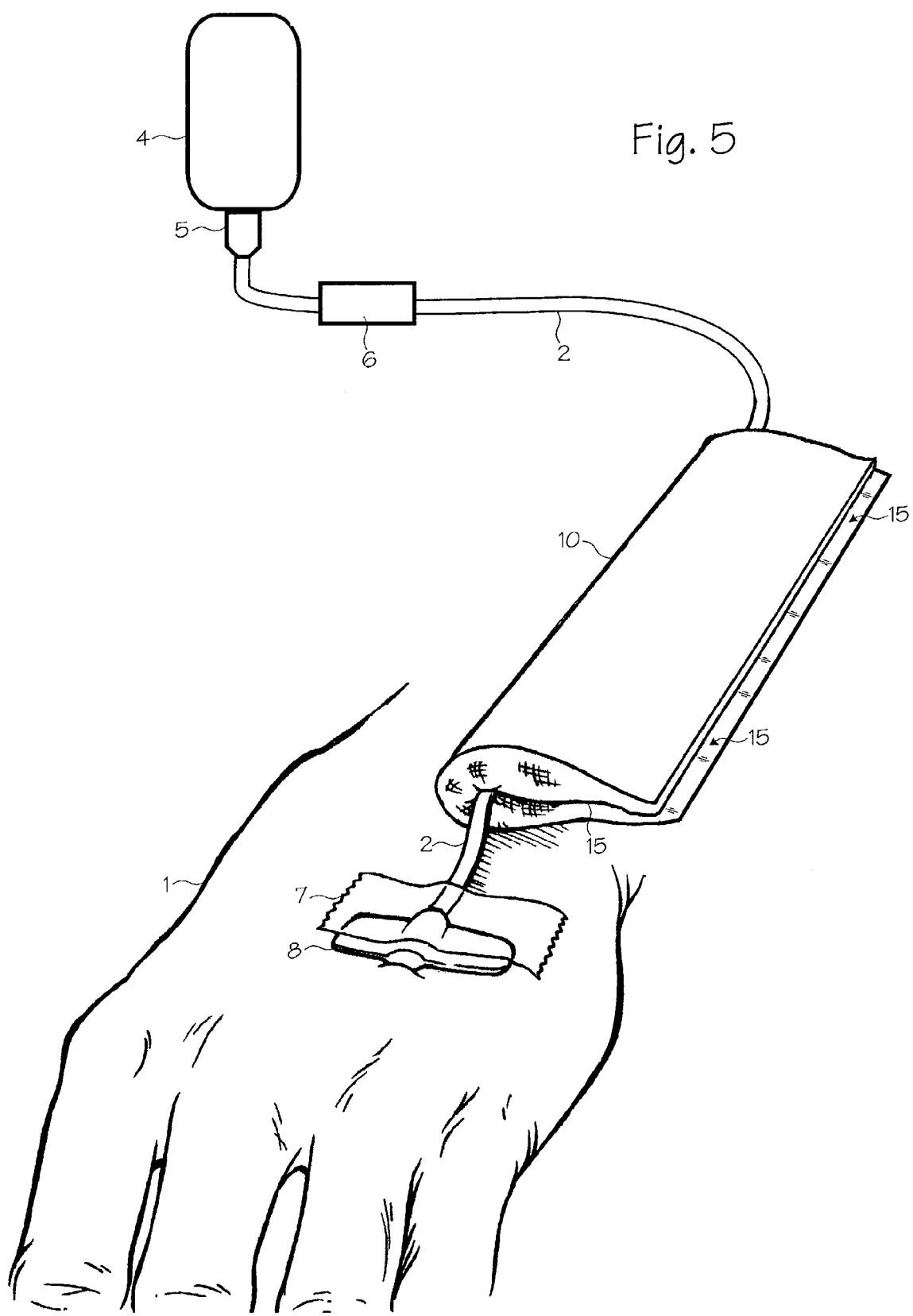
FIG. 5 shows an embodiment of the intravenous fluid warming and infusion system.

FIG. 5 shows an embodiment of the intravenous fluid warming and infusion system. In this embodiment the warming pouch is removed from the airtight package and is wrapped around the tube 2 without using a separate adhesive sheet. A portion of the outer surface of the warming pouch 10 is provided with an adhesive surface 15. A release paper, which is removed just prior to use, may be disposed on the adhesive surface. The warming pouch is secured to the tube by affixing the adhesive to the tube and by affixing the inner container to itself while being wrapped around the tube.

The warming device is employed when a patient is provided with intravenous fluids. The user removes the release paper from the adhesive sheet and also removes the warming pouch from the airtight package. The user places the warming pouch on the air-permeable adhesive sheet such that a strip of adhesive is exposed to either side of the warming pouch. Thus, the assembly is provided with a first strip of adhesive opposite a second strip of adhesive. The assembly is then wrapped around the tube with the warming pouch facing the tube, thereby heating any fluid disposed inside the tube. The assembly is secured to the tube by affixing the first adhesive strip to the second adhesive strip. The heating assembly may be disposed about 1 inch to about 2 inches (2.5 to 5 cm) proximally from the percutaneous point of insertion of the tube or needle to reduce heating losses. However, the assembly may be placed anywhere along the tube, in particular, it may be placed between the drip chamber and the roller clamp. After use, the warming assembly is disposed along with the IV tube.

In addition to providing comfort and therapeutic advantages, the warming device is small and light weight, being fractions of an ounce, and is thus easily transported. The warming device is readily useable under adverse conditions, such as emergency medical situations, and by emergency medical personnel. Indeed, the warming device can be applied in seconds anywhere an intravenous infusion is administered. The warming device is also compatible with any dialysis tubing used for dialysis or intravenous injections. The cost is nominal, being comparable to large surgical dressings.

Other types of flexible heating pouches, containers or pads may be used. For example, a warming pouch may hold an exothermic composition that produces a reaction when sufficiently agitated that produces heat. For example, a composition of iron, cupric carbonate, water soluble metal halide salt, citric acid and alkali metal chlorate may be mixed and agitated to produce heat. In use, the pouch is agitated to start the chemical reaction and is then wrapped and secured around the fluid delivery tube. In another embodiment, a warming pouch may hold a super-chilled liquid, such as sodium acetate, that warms to its freezing point when activated or agitated. (Such a pad is re-useable.) In use, the liquid is agitated to initiate a chain reaction of crystal growth that produces heat as the liquid changes to a solid. The pouch is then wrapped around the fluid delivery tube. In yet other embodiments, the warming pouch may hold a substance that retains heat well, such as water, flax seed or other substances. In use, the container is warmed and then wrapped and secured around the tube to warm the fluid in the tube. In any of these embodiments the warming pouch may be provided with one or more adhesive strips so that the pouch may be secured around the fluid delivery tube. Similarly, an adhesive sheet may be provided and the warming pouch disposed on the adhesive sheet to form a heating assembly.

In addition, multiple heating pouches may be placed along the IV tube, or on the IV bag or other fluid source, to provide extra heat. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A system for warming intravenous fluids, said system comprising:
    a tube suitable for providing intravenous fluids to a patient, said tube having a distal end adapted for insertion into a vein of a patient;
    a warming pouch comprising a flexible, air-permeable pouch wrapped around the tube;
    an exothermic composition disposed within the warming pouch, said exothermic composition capable of reacting with air to produce heat;
    an air-permeable adhesive sheet surrounding the warming pouch and extending beyond the warming pouch to provide an adhesive surface for securing the warming pouch around the tube.

2. The system of claim 1 wherein the warming pouch is disposed on the tube in a longitudinal region of the tube about 1 to 6 inches from the distal end of the tube.

3. The system of claim 1 further comprising:
    a drip chamber adapted to be connected in fluid communication with a fluid source and with the tube, said drip chamber disposed distally of the fluid source;
    a roller clamp disposed on the tube and further disposed distally of the drip chamber;
    wherein the warming pouch is disposed on the tube at a location distal to the drip chamber and roller clamp.

4. The device of claim 1 wherein the exothermic composition comprises a mixture of iron powder, cellulose, activated carbon, vermiculite and salt.

5. A device for warming a fluid to be provided intravenously to a patient, said device comprising:
    an inner container comprising a flexible, air-permeable container;
    an exothermic composition disposed within the inner container, said exothermic composition capable of reacting with air to produce heat;
    an adhesive sheet, wherein the inner container is disposed on the adhesive sheet to form a heating assembly comprising the inner container disposed on the adhesive sheet;
    a tube suitable for providing the fluid intravenously to the patient, wherein the fluid is disposed in the tube, and wherein the heating assembly is wrapped around the tube.

6. The device of claim 5 wherein:
    the adhesive sheet is larger than the inner container; and
    the inner container is placed on the adhesive sheet such that a portion of an adhesive on the adhesive sheet remains exposed.

7. The device of claim 5 wherein the heating assembly is disposed on the tube in a longitudinal region of the tube about 1 to 6 inches from the distal end of the tube.

8. The device of claim 5 wherein the exothermic composition comprises a mixture of iron powder, cellulose, activated carbon, vermiculite and salt.

9. A method of warming a fluid provided intravenously to a patient, wherein the fluid is provided through a tube, said method comprising the steps of:
    providing a device for warming a fluid to be provided intravenously to a patient, said device comprising:
        an inner container comprising a flexible, air-permeable container;
        an exothermic composition disposed within the inner container, said exothermic composition capable of reacting with air to produce heat;
        an adhesive sheet, wherein the inner container is disposed on the adhesive sheet to form a heating assembly comprising the inner container disposed on the adhesive sheet;
        a tube suitable for providing the fluid intravenously to the patient, wherein the fluid is disposed in the tube, and wherein the heating assembly is wrapped around the tube;
    exposing the inner container to air; and
    allowing the heating assembly to warm the fluid passing through the tube.

10. The method of claim 9 wherein the step of providing the device further comprises providing a device such that the heating assembly is disposed on the tube about 1 inch to about 2 inches from where the tube is percutaneously inserted into the patient.

11. A method of providing a fluid intravenously to a patient, said method comprising the steps of:
    providing a device for warming a fluid to be provided intravenously to the patient, said device comprising:
        an inner container comprising a flexible, air-permeable container;
        an exothermic composition disposed within the inner container, said exothermic composition capable of reacting with air to produce heat;
        an air permeable adhesive sheet, wherein the inner container is disposed on the adhesive sheet to form a heating assembly comprising the inner container disposed on the adhesive sheet;
        a tube suitable for providing the fluid intravenously to the patient, wherein the heating assembly is wrapped around the tube;
    providing a source of fluid and placing the source in fluid communication with the tube;

placing the tube in fluid communication with a vein of the patient through a percutaneous access point;
exposing the inner container to air;
delivering fluid to the patient through the tube.

12. The method of claim 11 wherein the step of providing the device further comprises providing a device such that the heating assembly is disposed on the tube about 1 to 6 inches from percutaneous access point when the tube is placed in fluid communication with the vein.

13. The method of claim 11 wherein the step of providing a device further comprises providing a hollow needle in fluid communication with the tube, and wherein the step of placing the tube in fluid communication with a vein of the patient comprises inserting the needle into a vein of the patient.

14. The method of claim 13 wherein the step of providing the device further comprises providing a device such that the heating assembly is disposed on the tube about 1 to 6 inches from the percutaneous access point.

15. A system for warming intravenous fluids, said system comprising:
   a tube suitable for providing intravenous fluids to a patient, said tube having a distal end adapted for insertion into a vein of a patient;
   a warming pouch comprising a flexible, air-permeable pouch wrapped around the tube;
   an exothermic composition disposed within the warming pouch, said exothermic composition capable of reacting with air to produce heat;
   an adhesive surface disposed on the warming pouch;
   wherein the warming pouch is folded around the tube and secured thereto by the adhesive.

16. The system of claim 15 wherein the warming pouch is disposed on the tube in a longitudinal region of the tube about 1 to 6 inches from the distal end of the tube.

17. The system of claim 15 further comprising:
   a drip chamber adapted to be connected in fluid communication with a fluid source and with the tube, said drip chamber disposed distally of the fluid source;
   a roller clamp disposed on the tube and further disposed distally of the drip chamber;
   wherein the warming pouch is disposed on the tube at a location distal to the drip chamber and roller clamp.

18. The system of claim 15 wherein the exothermic composition comprises a mixture of iron powder, cellulose, activated carbon, vermiculite and salt.

19. A method of warming a fluid provided intravenously to a patient, wherein the fluid is provided through a tube, said method comprising the steps of:
   providing a device for warming a fluid to be provided intravenously to a patient, said device comprising:
      a tube suitable for providing the fluid intravenously to the patient, wherein the fluid is disposed in the tube;
      a warming pouch comprising a flexible, air-permeable container, said warming pouch having an adhesive surface, said warming pouch being wrapped over the tube and secured thereto by the adhesive purpose;
      an exothermic composition disposed within the warming pouch, said exothermic composition capable of reacting with air to produce heat;
   exposing the warming pouch to air; and
   allowing the fluid to pass through the tube.

20. The method of claim 19 wherein the step of providing the device further comprises providing the device such that the warming pouch is disposed on the tube about 1 inch to about 2 inches from where the tube is percutaneously inserted into the patient.

21. A method of providing a fluid intravenously to a patient, said method comprising the steps of:
   providing a device for warming a fluid to be provided intravenously to the patient, said device comprising:
      a tube suitable for providing the fluid intravenously to the patient, wherein the fluid is disposed in the tube;
      a warming pouch comprising a flexible, air-permeable container, said warming pouch having an adhesive surface, said warming pouch being wrapped over the tube and secured thereto by the adhesive purpose;
      an exothermic composition disposed within the warming pouch, said exothermic composition capable of reacting with air to produce heat;
   providing a source of fluid and placing the source in fluid communication with the tube;
   placing the tube in fluid communication with a vein of the patient through a percutaneous access point;
   exposing the warming pouch to air;
   delivering fluid to the patient through the tube.

22. The method of claim 21 wherein the step of providing the device further comprises providing a device such that the heating assembly is disposed on the tube about 1 to 6 inches from percutaneous access point when the tube is placed in fluid communication with the vein.

23. The method of claim 21 wherein the step of providing the device further comprises providing a hollow needle in fluid communication with the tube, and wherein the step of placing the tube in fluid communication with a vein of the patient comprises inserting the needle into a vein of the patient.

24. The method of claim 23 wherein the step of providing the device further comprises providing the device such that the warming pouch is disposed on the tube about 1 to 6 inches from the percutaneous access point.

25. An intravenous infusion system comprising:
   an IV tube having a distal end adapted for insertion into a vein of a patient;
   a flexible pouch filled with an exothermic compound, said pouch being wrapped around the IV tube near the distal end of the IV tube;
   an air-permeable adhesive sheet surrounding the flexible pouch, said adhesive sheet being adhered to the flexible pouch to hold the pouch on the IV tube.

26. An intravenous infusion system comprising:
   an IV tube having a distal end adapted for insertion into a vein of a patient;
   a flexible pouch filled with an exothermic compound, said pouch being wrapped around the IV tube near the distal end of the IV tube, said flexible pouch having an adhesive surface securing the flexible pouch in place on the IV tube.

* * * * *